United States Patent [19]

Benson et al.

[11] Patent Number: 5,708,735
[45] Date of Patent: Jan. 13, 1998

[54] FIBER OPTIC DEVICE FOR SENSING THE PRESENCE OF A GAS

[76] Inventors: David K. Benson, 14154 W. First Dr.;
Clemens S. Bechinger, 35 S. Holman Way, # 3D, both of Golden, Colo. 80401; C. Edwin Tracy, 19012 W. 60th Dr., Golden, Colo. 80403

[21] Appl. No.: 624,112
[22] Filed: Mar. 29, 1996
[51] Int. Cl.⁶ .................................................. G01N 21/01
[52] U.S. Cl. .................................. 385/12; 356/445
[58] Field of Search ............... 385/12; 350/227.14, 350/227.18, 227.19, 227.23, 573; 73/23.2, 24.02; 356/445

[56] References Cited

U.S. PATENT DOCUMENTS

| | | | |
|---|---|---|---|
| 4,121,548 | 10/1978 | Hattori et al. | 123/32 |
| 4,294,801 | 10/1981 | Segawa et al. | 422/98 |
| 4,577,110 | 3/1986 | MacBride et al. | 250/461.2 |
| 4,836,012 | 6/1989 | Doty et al. | |
| 4,841,778 | 6/1989 | Butler et al. | |
| 4,929,049 | 5/1990 | Le Goullon et al. | |
| 4,931,851 | 6/1990 | Sibbald et al. | |
| 5,026,139 | 6/1991 | Klainer et al. | |
| 5,289,004 | 2/1994 | Okada et al. | 250/306 |
| 5,322,798 | 6/1994 | Sadowski | |
| 5,338,708 | 8/1994 | Felten | |
| 5,351,127 | 9/1994 | King et al. | |
| 5,417,821 | 5/1995 | Pyke | |

*Primary Examiner*—John D. Lee
*Assistant Examiner*—Ellen E. Kang
*Attorney, Agent, or Firm*—Edna M. O'Connor; Ken Richardson

[57] ABSTRACT

A fiber-optic device for sensing the presence of a gas in an environment is provided. The device comprises a light source for directing a light beam to a layer system having a first surface and a second surface opposite the first surface. The first surface is exposable to the light beam and the second surface is exposable to the environment. A first light portion encounters and reflects from the first surface at an angle of incidence free from optical wave guide resonance phenomenon and the second light portion encounters and reflects from the first surface at an angle of incidence enabling an optical wave guide resonance phenomenon. The layer system is selected to reversibly react with the gas to be detected. The reaction between the gas and the material changes the material's optical properties and the wavelength at which the optical wave guide resonance occurs. Furthermore, a mechanism for measuring the intensity of the reflected first light portion relative to the reflected second light portion is provided with the ratio of the first and second light portions indicating the concentration of the gas presence in the environment.

22 Claims, 2 Drawing Sheets

Fig. 1
Fig. 2
Fig. 3
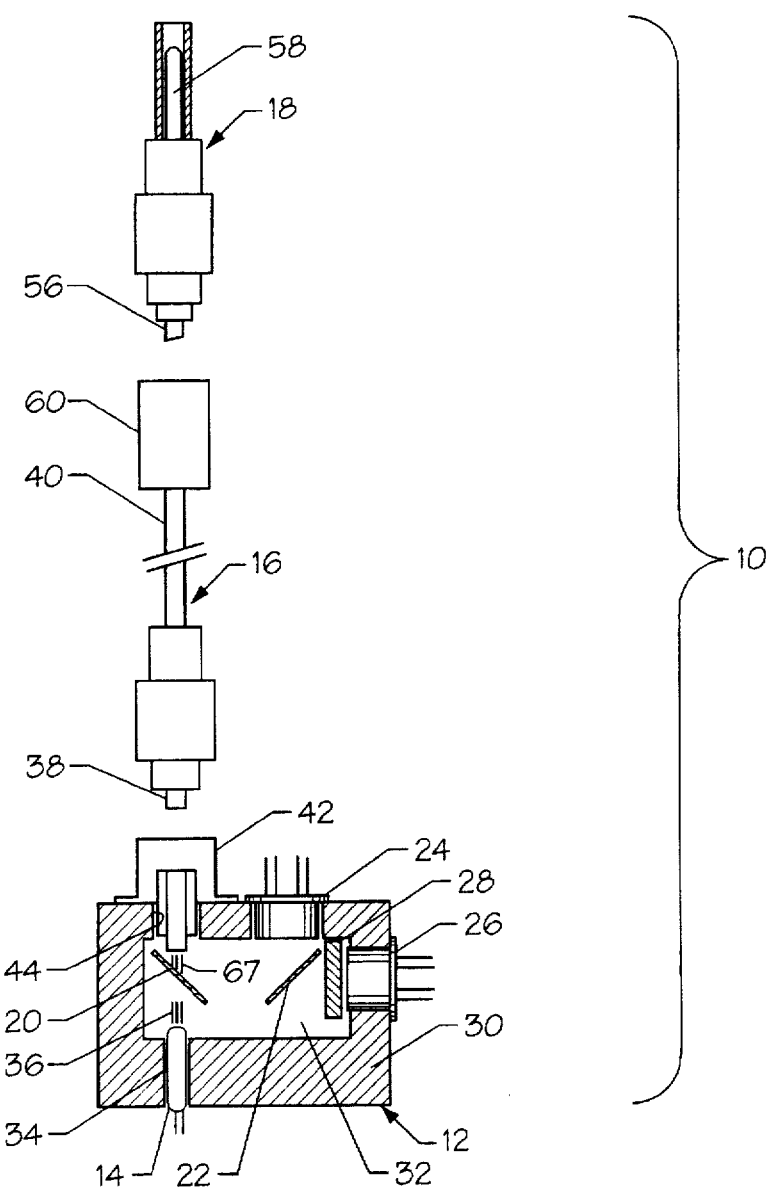
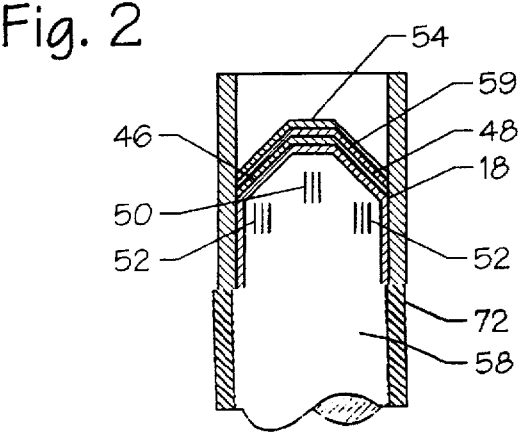
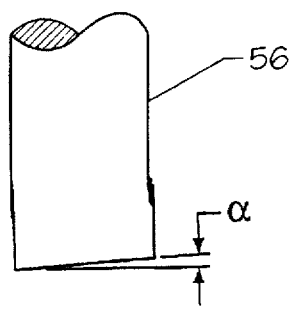

FIBER OPTIC DEVICE FOR SENSING THE PRESENCE OF A GAS

The United States Government has rights in the invention under Contract No. DE-AC36-83CH10093 between the United States Department of Energy and the National Renewable Energy Laboratory, a Division of the Midwest Research Institute.

BACKGROUND OF THE INVENTION

1. Field of the Invention

The present invention relates to an optical sensing device and, in particular, it relates to an optical sensing device which detects the presence of gas in an environment by measuring the relative intensity of light by utilizing an optical wave guide resonance phenomenon.

2. Description of the Prior Art

Many areas around the world suffer from poor and potentially dangerous air qualities directly related to vehicle emissions. In the United States, many communities are regulating the use of vehicles by mandating "no-drive" days and carpooling. Increasing public concern and regulatory pressure to reduce vehicular toxic gas emissions have motivated the U.S. automotive industry to improve gasoline engine performance and exhaust gas treatment dramatically over the last 20 years. Three-way catalysts and feedback control of air-to-fuel mixture ratio along with precise timing of multi-point fuel injectors are techniques now used to reduce automobile toxic exhaust gas emissions to less than 5% of what was common in 1975. Unfortunately, the growing number of automobiles and increased number of miles driven will require the industry to further reduce gasoline engine tailpipe toxic gas emissions during the next few decades while the country is making a gradual transition to less polluting fuels and zero-emission (i.e., electric powered) vehicles.

The need to reduce pollution while allowing people to maintain their vehicular freedoms has led people to create alternative fuel powered vehicles including hydrogen fueled vehicles. While maintaining the same explosive characteristics as gasoline, the very gaseous nature of hydrogen creates hazards which are not realized with gasoline. The hazards of using hydrogen fuel in vehicles require extensive safety precautions including hydrogen leak detection. Recent unpublished hazard analyses for Ford Motor Company by Directed Technologies, Inc. identified the situation of a hydrogen fuel leak in a garaged automobile as a particularly serious hazard requiring reliable, on-board hydrogen leak detection.

Hydrogen leak detectors are commercially available. Even compact hydrogen detectors, however, are typically too complex, bulky and expensive for widespread use in hydrogen-fueled vehicles. Additionally, since conventional detectors require electrical wiring for control and signal transmission, the detectors themselves also present a possible hydrogen leak ignition hazard.

In the art, Sadowski, U.S. Pat. No. 5,322,798, describes a certain type of gas detector utilizing surface plasmon resonance (SPR). Generally, the surface plasmon is a particular kind of electromagnetic wave which propagates along the surface of a metal. Optical excitation of the surface plasmon can be achieved if a p-polarized, collimated light beam undergoes total reflection at the surface of a glass substrate coated with a thin metal film. If the momentum component of photons parallel to the surface matches a particular value, a corresponding component of momentum of the surface plasmons on the opposite surface of the metal film can be excited. This occurs for a given wavelength at a given incidence angle (the resonance angle) of light. If white light is used, the phenomenon is observed as a sharp minimum in the spectrum of the reflected light at a particular wavelength where surface plasmons are excited. The wavelength at which this dip occurs depends decisively on the properties of the surface layer on top of the metal film, and therefore, the phenomenon can be used to monitor changes on this surface layer caused, e.g., by a specific chemical or biological reaction or by the change of concentration of some substance in the immediate vicinity of this surface.

In the Sadowski patent, a method is described for using a surface plasmon resonance to carry out a measurement of adsorbed gases. The Sadowski patent's method includes directing a beam of electromagnetic radiation through a transparent dielectric material onto a first surface of a metal layer. The second surface of the metal layer, opposite the first surface, contacts a test substance such as air that contains a substance to be detected. A change in the intensity of the reflected radiation at the resonance wavelength or a change in the angle at which the resonance occurs, indicate that a change has occurred at the interface between the metal layer and the test substance such as the incorporation/adsorption of the substance to be measured in/onto the metal. The changes in wavelength and angle of incidence where the resonance occurs are correlated with concentration of the substance to be detected.

While able to detect hydrogen gas, the device of the Sadowski patent would not be very suitable for detecting hydrogen leaks in vehicles. The Sadowski patent's device is non-selective in that the device responds to any gas which adsorbs to the metal surface. Hydrogen and helium gas as well as carbon dioxide are detected by the Sadowski patent's device. Since both helium and carbon dioxide naturally occur in our environment, carbon dioxide especially in traffic congestion situations, the lack of selectivity severely limits the use of the Sadowski patent's device for leak detection in vehicles. Furthermore, the Sadowski patent fails to correct for drift in the characteristics of the sensor and optical components. If the sensor and/or the optical components in the device of the Sadowski patent change their properties or otherwise become defective, there would be no way to determine the true readings of the test material since there is no reference beam present to standardize the test.

Additionally, surface plasmon resonance phenomenon are very sensitive to any kind of adsorbed impurities/adsorbates on the metal layer. Any adsorbent layers, e.g., water, on the Sadowski patent's sensor device shifts the wavelength at which the surface plasmon resonance occurs. Therefore, the device of the Sadowski patent would not be beneficial for detecting hydrogen gas in many environments due to the sensitivity of the sensor device to other materials.

SUMMARY

The present invention is a device for sensing the presence of a gas in an environment. The device comprises a light source creating a light beam having a first light portion and a second light portion. The device further comprises a layer system having a first surface and a second surface opposite the first surface. The first surface is exposable to the light beam from the light source and the second surface is exposable to the environment.

In addition, the device comprises means for directing the first and second light portions of the light beam with the first light portion encountering the first surface at an angle of incidence free from optical wave guide resonance phenomenon and the second portion encountering the first surface at an angle of incidence enabling an optical wave guide resonance phenomenon. Finally, the device comprises means for measuring the intensity of the first light portion relative to the second light portion. The first and second light portions reflect from the first surface of the layer system such that gas presence in the environment is determined by comparing the intensity of the first light portion relative to the second light portion.

In a preferred embodiment, the gas to be detected is hydrogen and the light source comprises a white light source. Furthermore, preferably, the layer system comprises transition metal oxides and their oxysalts and a high conductivity metal wherein the transition metal oxide or oxysalt is selected from the group consisting of $WO_3$, $Nb_2O_3$ and $CoMoO_4$ and the high conductive metal is selected from the group consisting of gold, silver, platinum, and palladium. The layer system can further comprise a fluorinated hydrocarbon polymer and a catalytic material wherein the fluorinated hydrocarbon polymer comprises TEFLON.

In another preferred embodiment, the directing means comprise a fiber optic sensor having a length, a proximal end and a distal end. The proximal end receives the light beam from the light source and the light beam travels the length of the fiber optic sensor to the distal end. The directing means further comprise the distal end of the fiber optic sensor having a first facet, a second facet and a third facet with the layer system being applied to each of the facets. The first facet is preferably substantially perpendicular to the light beam with the first light portion contacting the first facet at an angle of incidence free from optical wave guide resonance phenomenon. The second and third facets are preferably offset approximately 45° from the first facet and the light beam with the second light portion contacting the second and third facets at an angle of incidence enabling optical wave guide resonance phenomenon. The second and third facets are preferably substantially opposite each other with the second light portion reflecting from either the second or third facet to the other respective facet. A protective sleeve surrounds the distal end of the fiber optic sensor with the sleeve mounted to the fiber optic sensor and extending beyond the distal end.

In yet another preferred embodiment, the measuring means comprise at least one partially reflective mirror, a first photoamplifier and a second photoamplifier at the proximal end of the optical fiber. Each mirror reflects a first part of the first and second light portions to the first photoamplifier. The second photoamplifier receives a second part of the first and second light portions with the second part passing through the mirror.

In another preferred embodiment, the sensing device comprises an optical filter. The filter is positioned between the mirror and the second photoamplifier with the filter transmitting only wavelengths of light that are normally absorbed by the optical wave guide resonance phenomenon in the absence of the gas to be detected.

The present invention further includes a method for sensing the presence of a gas in an environment. The method comprises, first, providing a layer system having a first surface and a second surface. Second, the second surface of the layer system is exposed to the environment. Third, a light source is directed to the first surface of the layer system with the light source having a first light portion and a second light portion. The first light portion encounters the first surface at an angle of incidence free from optical wave guide resonance phenomenon and the second light portion encounters the first surface at an angle of incidence enabling an optical wave guide resonance phenomenon. Fourth, the intensity of the first light portion is measured relative to the second portion after the first and second light portions reflect from the first surface of the layer system. Finally, the first light portion is compared relative to the second light portion to determine the presence of gas in the environment.

In a preferred embodiment, the gas to be detected is hydrogen and the light source comprises a white light source. Furthermore, preferably, the layer system comprises transition metal oxides, high conductive metal and a fluorinated hydrocarbon polymer with the transition metal oxides being selected from the group consisting of $WO_3$, $Nb_2O_3$, and $CoMoO_4$, and related materials, the high conductive metal being selected from the group consisting of gold and silver, and the fluorinated hydrocarbon polymer comprises TEFLON and related polymers.

BRIEF DESCRIPTION OF THE DRAWINGS

FIG. 1 is a side view of the sensing device of the present invention illustrating a fiber optic sensor having a housing, an optic fiber, a sensing element, a pair of reflective mirrors, a pair of photoamplifiers and an optical filter;

FIG. 2 is a section view of the sensing element of the sensing device of the present invention illustrating a sensing end of a sensor probe, a layer system comprising a metal coating, a transition metal oxide and a fluorinated hydrocarbon polymer, and a protective sleeve;

FIG. 3 is a side view of a connection end of the sensor probe of the present invention illustrating an angle to inhibit reflection;

DETAILED DESCRIPTION OF THE PREFERRED EMBODIMENTS

Figure 4:
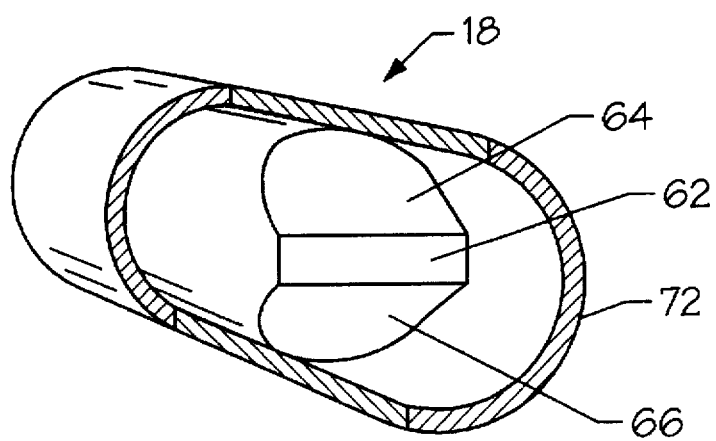
FIG. 4 is a perspective view of the sensing element of the sensing device of the present invention.

The present invention is a sensing device, indicated generally at 10, for detecting the presence of gas in an environment. While the sensing device 10 of the present invention can detect different types of gas in any environment, including, but not limited to, buildings, chemical process plants, refineries, etc., the construction and design of the sensing device 10 especially suits the sensing of hydrogen leaks in hydrogen-fueled vehicles or similar applications. Therefore, in discussing the sensing device 10 of the present invention in the present application, Applicants will particularly describe the sensing device 10 in conjunction with vehicle use. It should be noted, however, that other uses of the sensing device 10 are envisioned and within the scope of the present invention.

The sensing device 10 of the present invention differs significantly from the detectors set forth above in that the sensing device 10 of the present invention utilizes an optical wave guide resonance phenomenon to determine the presence of a gas in an environment rather than a simple surface plasmon resonance. The optical wave guide resonance phenomenon differs from simple surface plasmon resonance in that for optical wave guide resonance, an additional thin, dielectric film material is deposited on the metal coating. The dielectric film material generally has a higher index of refraction than the material/gas on its surface. The guided wave resonance occurs as the evanescent light wave travels through the metal coating and excites the guided wave in the adjacent dielectric film material. The film material forms a wave guide for light intersecting the interface at an angle just above the critical angle. Any reactions between the dielectric film and the gas to be detected causes a change in the optical dielectric constants of the dielectric film. The changes in the optical constants of the dielectric film, in turn, shift the wavelength at which the optical wave guide resonance occurs.

As illustrated in FIG. 1, in the present invention, the sensing device 10 comprises a housing 12, a light source 14, an optical fiber 16, a sensor probe 18, first and second partially reflective mirrors 20, 22, first and second photo-amplifiers or photoresistors 24, 26, and an optical filter 28. The housing 12 is constructed and sized to be mounted within a vehicle (not shown) and comprises an outer wall 30 surrounding an inner chamber 32. The outer wall 30 is preferably constructed from a durable material, such as aluminum, to withstand a potentially rigorous vehicle environment. Other materials can be used for the housing 12, including, but not limited to, other metals and metal alloys, plastics or ceramics.

The light source 14 of the present invention is mounted within an illumination opening 34 in the housing 12. The illumination opening extends through the outer wall 30 of the housing 12 to the inner chamber 32 of the housing and is sized and constructed to accommodate at least a portion of the light source 14 such that the light source 14 directs a light beam 36 into the inner chamber 32 of the housing 12.

In contrast to surface plasmon resonance, guided waves are excitable with both s-polarized and p-polarized light. Therefore, the light beam 36 generated by the light source 14 can be either polarized or nonpolarized. Having either a polarized or nonpolarized light source 14 gives the sensing device 10 of the present invention a distinct advantage in that such light sources are generally very inexpensive. For instance, in the present invention, the light source 14 is preferably a white light source such as, but not limited to, a halogen lamp or a tungsten filament lamp.

The sensing device 10 of the present invention further comprises an optical fiber 16 having a housing connection end 38 and a sensor connection end 40. The optical fiber 16 is connected to the housing 12 at the housing connection end 38 by a first connection element 42. The housing connection end 38 of the optical fiber 16 extends into the housing 12 through an optical fiber opening 44 extending through the outer wall 30 to the inner chamber 32 and is positioned substantially opposite the illumination opening 34 such that the optic fiber 16 receives substantially the entire light beam 26 of the light source 14.

The optical fiber 16 of the sensing device 10 of the present invention is preferably a single, continuous polymer optical fiber patch cord. It should be noted, however, that any type of optical fiber 16 is within the scope of the present invention provided that the light beam 36 is transmittable along the length of the optical fiber 16 from the housing connection end 38 to the sensor connection end 40.

While the optical fiber 16 of the present invention has been described as being a singular, continuous fiber, it is within the scope of the present invention to have several sections of optical fiber 16 connected to each adjacent section by a series of optical fiber connectors (not shown). Using several sections of the optical fiber 16 provides greater ability to detect gases at different sites.

As illustrated in FIG. 2, the sensing device 10 of the present invention additionally comprises the multimode optic fiber sensor probe 18 having a connection end 56 and a sensing end 58. The sensing end 58 is covered by a thin metal coating 46 having a high conductivity, as set forth above. A film material 48 is deposited on the metal coating 46 to allow for wave guide resonance phenomenon to occur since, as set forth above, the wave guide resonance is dependent on the optical dielectric constant of the film material 48 rather than simply on the interfaces of the metal coating 46. In fact, the sensing device 10 of the present invention is unique in that the sensor probe 18 of the present invention directs the light beam 36 such that a first portion 50 of the light beam 36 encounters the sensor probe at an angle of incidence free from optical wave guide resonance phenomenon and a second portion 52 of the light beam 36 encounters the sensor probe at an angle of incidence enabling an optical wave guide resonance phenomenon.

In the present invention, the metal coating 46 preferably comprises Au (gold) or Ag (silver) and the film material 48 preferably comprises transition metal oxides or their oxy-salts including, but not limited to, $WO_3$, $Nb_2O_3$ and $CoMoO_4$. The transition metal oxides and their oxysalts are generally used as catalysts for oxidative chemical processing of gas-phase chemicals. In general, their optical properties are changed by the changes in the metal oxidation state during the catalysis. The reversible reduction of the $WO_3$ film material, for example, by hydrogen strongly affects the optical properties and guided wave resonance because the hydrogen introduces mixed valence states in the $WO_3$. Optical transitions between adjacent metal ions of different oxidation states in the presence of hydrogen cause a strong, broad optical absorption band centered at about 1.2 eV and a large change in the real part of the optical dielectric constant. A very small change, i.e., one percent, in the optical dielectric constant of the $WO_3$ causes a strong and readily measured shift in the wavelength of the guided wave resonance. When the $WO_3$ is exposed to hydrogen in pressures as low as 100 parts per million, the change in the optical dielectric constant occurs. Properly deposited film material such as $WO_3$ has a microporous morphology and exhibits fast response time constants of less than 0.1 second at room temperature which makes $WO_3$ well suited for safe detection of a hydrogen leak. Faster responses occur at temperatures above room temperature.

Protection of the film material 48 from water and other contaminants is important for the accurate detection of gas in an environment. Therefore, a fluorinated hydrocarbon polymer 54 is applied to the film material 48 to inhibit water or other contaminants from reaching and condensing on the film material 48. The polymer (sometimes referred to as TEFLON) 54 is an ideal protectent since the polymer 54 provides a barrier for contaminants but allows gas molecules to pass through the polymer 54 to reach the film material 48 and thereby be sensed by the sensing device 10.

Figure 5:
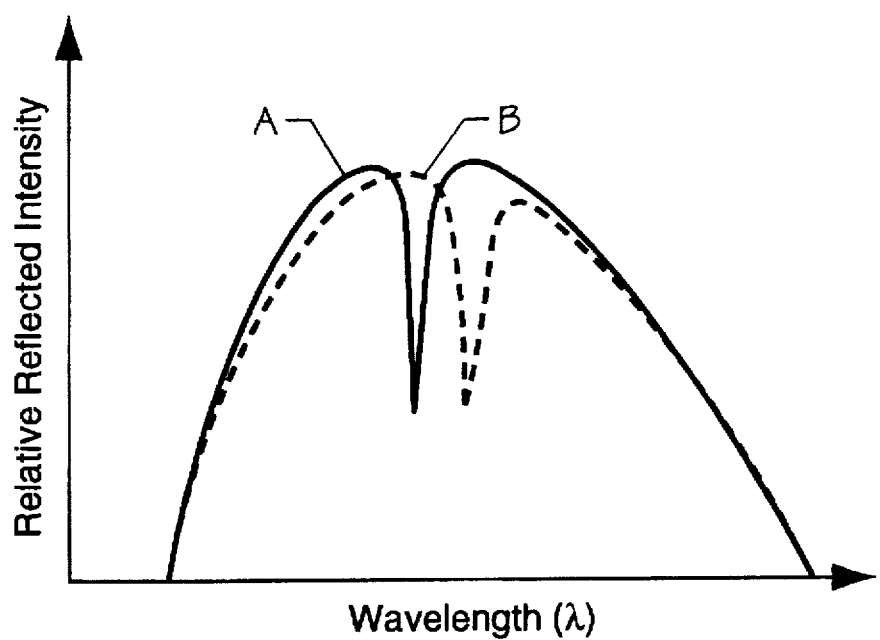
FIG. 5 is a graph illustrating the relative reflected intensity versus the wavelength with the solid line illustrating the reflected light spectrum and illustrating the guided surface wave resonant absorption at A when no hydrogen is present in the environment. The dotted line illustrates the shift in the wavelength of the guided surface wave resonant absorption to B when hydrogen is present in the environment.

In a preferred embodiment of the sensing device 10 of the present invention, the metal coating 46 comprises Au having a thickness of approximately 49 nm, the film material 48 comprises $WO_3$ having a thickness of approximately 150 nm and the polymer 54 comprises TEFLON having a thickness of approximately 100 nm. As illustrated in FIG. 5, the materials and actual thicknesses of the film material 48 are selected to exhibit resonant guided wave absorption at different wavelengths across the visible spectrum. Line A illustrates the relative reflected intensity versus the wavelength when no hydrogen is present in the environment. Line B, shown in phantom, illustrates the relative reflected intensity versus the wavelength when hydrogen is present in the environment.

Since the present invention has been designed to operate as a guided wave resonance, the resonant frequency electromagnetic wave is guided along the $WO_3$ film material and interacts with the bulk of the $WO_3$ film material rather than just with the material at the interface. When hydrogen is present, the hydrogen spontaneously reacts with the $WO_3$. The optical dielectric properties of the $WO_3$ change and the resonance frequency and amplitude of the guided wave resonance change. The spontaneous reaction of hydrogen with the $WO_3$ is sufficient to cause a strong shift in the guided wave resonance, thereby signaling the presence of hydrogen in the air. It should be noted that a very small amount of catalyst 59 applied on the $WO_3$ surface increases the reaction in the $WO_3$ significantly.

The connection end 56 of the sensor probe 18 is connected to the sensor connection end 40 of the optical fiber 16 by a second connection element 60. As illustrated in FIG. 3, the connection end 56 of the sensor probe 18 can be slightly angled to inhibit reflection back into the detector photoamplifiers 24, 26. To optimize efficiency, preferably, the angle α is approximately eight degrees.

As illustrated in FIGS. 2 and 4, the sensing end 58 of the sensor probe 18 preferably comprises a retroreflective blunt-tipped chisel shape having a flat end facet 62, a first angled facet 64 and a second angled facet 66 at approximately 45° angles to the flat end facet 62 and to the direction of the light beam 36. Having both the flat end facet 62 and the first and second angled facets 64, 66 are important in the operation of the present invention as a gas detector. The 45° angled facets 64, 66 create a retro-reflection that returns the incident light to the detectors after two resonance absorptions (one at each 45° facet).

As mentioned, the dielectric film material 48 is deposited on the flat end facet 62 and the first and second angled facets 64, 66 of the sensor probe 18. Most of the light propagating to the sensor probe 18 is reflected at either the flat face facet 62 and both the first and second angled facets 64, 66 and returns back through the optic fiber 16 toward the housing 12 as a reflected light beam 67. In sum, the light beam 36 strikes the flat face facet 62 at an angle of incidence free from optical wave guide resonance phenomenon and strikes the first and second angled facets 64, 66 at an angle of incidence enabling an optical wave guide resonance phenomenon.

Deposition of the film material 48 can be accomplished by various techniques including, but not limited to, thermal evaporation, rf- and dc-sputtering and laser ablation. Since stoichiometry is an important parameter in the reactivity of the film material 48, depositions are preferably conducted in a controlled partial pressure chamber in which the gas composition is carefully controlled.

As illustrated in FIGS. 2 and 4, a protective sleeve 72 is preferably attached to the second connection element 60, positioned about the sensor probe 18 and extending beyond the facets 62, 64, 66. Assuming, arguendo, that the sensing device 10 is used for detecting hydrogen leaks in a hydrogen-fueled vehicle, in order to detect such leaks, the sensor probe 18 of the sensing device 10 must be positioned adjacent the potential leak source. In many instances, the potential leak sources are located in a rough and rugged environment, i.e., either under the vehicle or in or about the vehicle engine. The sleeve 72 protects the sensor probe 18 from these or any other environmental hazard associated with any intended use of the sensing device 10 of the present invention. It should be noted that the TEFLON polymer 54 layer can also be placed at the end of the sleeve 72 instead of being applied to the film material 48 so long as the polymer 54 still provides a barrier to contaminants.

As illustrated in FIG. 1, the sensing device 10 further comprises the pair of light beam splitters or a partially reflecting first mirror 20 and a partially reflecting second mirror 22 mounted within the inner chamber 32 of the housing 12 to receive the reflected light beam 67 traveling toward the mirrors 20, 22 from the sensor probe 18. In the preferred embodiments, the first and second mirrors 20, 22 are designed to reflect approximately 50% of the reflected light beam 67 directed at the first and second mirrors 20, 22. Therefore, in operation, the first mirror 20 receives the reflected light beam 67 transmitted back from the sensing probe 18 and directs at least a portion of the reflected light beam 67 toward the second mirror 22. It should be noted that since the first mirror 20 is a partially reflecting mirror thereby not only reflecting 50% of the reflected light beam 67, but also allowing 50% of the reflected light beam 67 to pass through the first mirror 20, the first mirror 20 can be positioned such that the reflected light beam 67 strikes the first mirror 20 prior to entering the optical fiber 16.

The physical optics of wave guide resonance are generally calculated using the Fresnel equations and known optical properties and thicknesses of the film material. The reflected light beam 67 striking the flat face facet 62 creates a reflected reference beam that is not affected by the gas reactions with the coating because the beam strikes the flat face facet 62 at the incorrect angle of incidence for resonance. In the present invention, only the retro-reflected light beam from the first and second angled facets 64, 66 contain information about the resonance in the form of resonance wavelength and amplitude. A portion of the total reflected light is collected by the first photoamplifier 24 as a reference beam. Only the portions of the reflected beam having wavelengths close to the resonance wavelength pass through optical filter 28 and reach the second photoamplifier 26. The first photoamplifier 24 is preferably a photodiode and mounted to the housing 12 such that the first photo amplifier 24 receives a reflected portion 68 of the reflected light beam 67 which is reflected from the second mirror 22. The second photoamplifier 26 is also a photodiode and is mounted to the housing 12 such that the second photoamplifier 26 receives an unreflected portion 70 of the reflected light beam 67 which passes through the second mirror 22. It should be noted that while the first and second photoamplifiers 24, 26 have been described as photodiodes, any type apparatus which senses light and provides an output signal correlated to the incident of the light intensity is within the scope of the present invention.

The second photoamplifier 26 includes a narrow bandpass optical filter 28 so that it responds only to the light in the wavelength range of the guided surface wave resonance. The filter 28 allows passage of only the wavelengths of the reflected light beam 67 which are normally absorbed by the surface plasmon resonance. When gas is present, the resonance wavelength changes so that less light is absorbed in the wavelengths that can pass through the filter. Consequently, more light strikes the second photoamplifier 26 and the gas detector signal increases.

The first photoamplifier 24 produces a first output signal (PA1) and the second photoamplifier 26 produces a second output signal (PA2). The first and second output signals from the first and second photoamplifiers 24, 26, respectively, are adjusted to be approximately equal in the absence of hydrogen. The first and second output signals are electronically divided to produce a ratio signal proportional to PA2/PA1. When hydrogen is present, the surface plasmon resonance wavelength shifts so that more light passes through the band-pass filter thereby increasing the signal from the second photoamplifier 26 and ratio signal PA2/PA1. Comparing the signal intensities cancels out all variations except the variations caused by the presence of gas in the environment.

The sensing device 10 of the present invention can be used to detect hydrogen leaks in numerous locations about the vehicle with only requiring additional optic fibers 16 and sensor probes 18. The housing 12, the first and second mirrors 20, 22, the first and second photoamplifiers 24, 26, and the optical filter can be positioned in a centralized, convenient location either within or outside the vehicle occupant compartment. The multiple optic fibers 16 extend from the housing 12 to position the multiple sensor probes 18 adjacent various potential leak locations throughout the undercarriage and engine compartment of the vehicle. The light source 14 is positioned to direct the light beam 36 into each of the optic fibers 16 or several light sources 14 can be provided. When a leak occurs, the no-hydrogen-present signals from the affected sensor probe 18 will change to indicate a hydrogen leak in accordance with the above whereby the control electronics will indicate which sensor probe 18 is affected and sound an alarm, otherwise notify vehicle occupants and execute whatever safety measures such as shutting valves or starting ventilation fans as are needed.

Furthermore, the sensing device 10 of the present invention can also be used to detect any number of gases using only one sensor probe 18 having a pair of angled facets for each gas to be detected. For example, to detect three gases, the sensor probe would have three angled pairs or six angled facets. If the sensitivity of sensor angled facet pair number one to gas A is a1 and to gas B is b1 and to gas C is c1, the total resonant absorption signal associated with that single angled facet pair will be:

$$S1 = a1(A) + b1(B) + c1(C)$$

and similarly with sensor angled facet pair number two and angled facet pair number three. More generally, the set of signals from n angled facets can be interpreted in terms of n linear equations:

$$S_i = f_{1i}(X1) + f_{2i}(X2) + \ldots f_{ni}(X_m)$$

from which the m unknown gas component concentrations can be readily obtained. With a sensor design having more angled facet pairs than gases to be measured, there would be some redundancy that would help to resolve otherwise ambiguous solutions to the equation set.

The sensing device 10 of the present invention provides a flexible and low-cost means of monitoring numerous locations where hydrogen gas leaks could pose a safety hazard. The removal of all electrical connections to a central location remote from the actual sensor probe 18 reduces the costs of electrical wiring and maintenance and eliminates safety problems associated with electrical failures possibly becoming hydrogen ignition sources.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

We claim:

1. A device for sensing the presence of a gas in an environment, the device comprising:

a light source creating a light beam having a first light portion and a second light portion;

a layer system having a first surface and a second surface, the second surface being opposite the first surface, the first surface exposable to the light beam from said light source, the second surface exposable to the environment;

means for directing the first and second light portions of the light beam, the first light portion encountering and reflecting from the first surface at an angle of incidence free from optical wave guide resonance phenomenon, the second portion encountering and reflecting from the first surface at an angle of incidence enabling an optical wave guide resonance phenomenon; and means for measuring the intensity of the reflected first light portion relative to the reflected second light portion whereby gas presence in the environment is determined by comparing the intensity of the first light portion relative to the second light portion.

2. The device of claim 1 wherein the gas is hydrogen.

3. The device of claim 1 wherein the layer system comprises a first layer comprising a high conductive metal having an inner surface and an outer surface, and a second layer comprising a transition metal oxide or oxysalt having an inner surface and an outer surface, the inner surface of the transition metal oxide or oxysalt being applied on the outer surface of the high conductive metal, the inner surface of the high conductive metal exposable to the light beam, the outer surface of the transition metal oxide or oxysalt exposable to the environment.

4. The device of claim 3 wherein the transition metal oxide or transition metal oxysalt is selected from the group consisting of $WO_3$, $Nb_2O_3$ and $CoMoO_4$.

5. The device of claim 3 wherein the high conductive metal is selected from the group consisting of gold, silver, platinum and palladium.

6. The device of claim 3 wherein the layer system further comprises a fluorinated hydrocarbon polymer applied to the outer layer of the transition metal oxide or oxysalt.

7. The device of claim 6 wherein the fluorinated hydrocarbon polymers comprise TEFLON.

8. The device of claim 3 wherein the layer system further comprises a catalyst material applied to the outer surface of the transition metal oxide or oxysalt.

9. The device of claim 1 wherein the directing means comprise a fiber optic sensor having a length, a proximal end and a distal end, the proximal end receiving the light beam from the light source, the light beam traveling the length of the fiber optic sensor to the distal end.

10. The device of claim 9 wherein the directing means further comprise the distal end of the fiber optic sensor having a first facet, a second facet and a third facet, the layer system being applied to each of the facets, the first facet being substantially perpendicular to the light beam, the first light portion contacting the first facet at an angle of incidence free from optical wave guide resonance phenomenon, the second and third facets being offset approximately 45° from the first facet and the light beam, the second light portion contacting the second and third facets at an angle of incidence enabling optical wave guide resonance phenomenon, all facets providing retro-reflection back toward the proximal end of the fiber optic sensor.

11. The device of claim 10 wherein the second and third facets are substantially opposite each other, the second light portion reflecting from either the second or third facet to the other respective facet, the reflecting second light portion providing a doubling of the optical wave guide resonance absorption.

12. The device of claim 9 and further comprising a sleeve about the distal end of the fiber optic sensor, the sleeve mounted to the fiber optic sensor and extending beyond the distal end.

13. The device of claim 1 wherein the measuring means comprise at least one partially reflective mirror, a first photoamplifier and a second photoamplifier, the mirror reflecting a first part of the first and second light portions to the first photoamplifier, the second photoamplifier receiving a second part of the first and second light portions, the second part passing through the mirror.

14. The device of claim 13 and further comprising an optical filter, the filter positioned between the mirror and the second photoamplifier, the filter transmitting only wavelengths of light approximately equal to the wavelength of the optical wave guide resonance phenomenon.

15. A method for sensing the presence of a gas in an environment, the method comprising:

providing a layer system having a first surface and a second surface;

exposing the second surface of the layer system to the environment;

directing a light source to the first surface of the layer system, the light source having a first light portion and a second light portion, the first light portion encountering and reflecting from the first surface at an angle of incidence free from optical wave guide resonance phenomenon, the second light portion encountering and reflecting from the first surface at an angle of incidence enabling an optical wave guide resonance phenomenon;

measuring the intensity of the reflected first light portion relative to the reflected second portion; and comparing the reflected first light portion relative to the reflected second light portion to determine the presence of gas in the environment.

16. The method of claim 15 wherein the gas is hydrogen.

17. The method of claim 15 wherein the layer system comprises a first layer comprising a high conductive metal having an inner surface and an outer surface, and a second layer comprising a transition metal oxide or oxysalt having an inner surface and an outer surface, the inner surface of the transition metal oxide or oxysalt being applied on the outer surface of the high conductive metal, the inner surface of the high conductive metal exposable to the light beam, the outer surface of the transition metal oxide or oxysalt exposable to the environment.

18. The method of claim 17 wherein the transition metal oxide or transition metal oxysalt is selected from the group consisting of $WO_3$, $Nb_2O_3$ and $CoMoO_4$.

19. The method of claim 17 wherein the high conductive metal is selected from the group consisting of gold, silver, platinum and palladium.

20. The method of claim 17 wherein the layer system further comprises a fluorinated hydrocarbon polymer applied to the outer surface of the transition metal oxide or oxysalt.

21. The method of claim 20 wherein the fluorinated hydrocarbon polymer comprises TEFLON.

22. The method of claim 17 wherein the layer system further comprises a catalyst material applied to the outer surface of the transition metal oxide or oxysalt.

* * * * *